United States Patent

Clark et al.

Patent Number: 4,533,499
Date of Patent: Aug. 6, 1985

[54] PROCESS FOR THE PRODUCTION OF TRIARYL METHANE COMPOUNDS

[75] Inventors: Malcolm C. Clark, Cheadle; John B. Henshall, Manchester; Derrick A. Hart, Rochdale, all of England

[73] Assignee: Ciba-Geigy Corporation, Ardsley, N.Y.

[21] Appl. No.: 597,213

[22] Filed: Apr. 6, 1984

Related U.S. Application Data

[63] Continuation of Ser. No. 232,081, Feb. 6, 1981, abandoned.

[30] Foreign Application Priority Data

Feb. 14, 1980 [GB] United Kingdom ................ 8005014
Oct. 10, 1980 [GB] United Kingdom ................ 8032773

[51] Int. Cl.³ .................... C07D 405/2; C07D 307/83; C09B 11/10
[52] U.S. Cl. .................................. 260/391; 544/58.7; 544/86; 544/357; 546/190; 548/456; 548/518; 549/309; 564/61; 260/390
[58] Field of Search ....................... 548/456; 546/190; 260/390, 391; 544/86, 35.7, 58.7

[56] References Cited

U.S. PATENT DOCUMENTS

Re. 23,024  8/1948  Adams ................................ 549/309
2,726,252  12/1955  Balon et al. ......................... 260/391
3,995,088  11/1976  Garner et al. ...................... 282/27.5

FOREIGN PATENT DOCUMENTS 1325029  8/1973  Fed. Rep. of Germany ....... 549/309

OTHER PUBLICATIONS

Yoshino: Repts. Tokio Imp. Ind. Research Inst. Lab., 37, 95–189, (1942), Complete English Translation and Chem. Abstr. 42, 5887.

*Primary Examiner*—Richard L. Raymond
*Assistant Examiner*—D. B. Springer
*Attorney, Agent, or Firm*—Edward McC. Roberts; Kevin T. Mansfield

[57]  ABSTRACT

A process for the production of a compound of formula

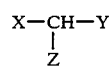
(1)

which comprises reacting a compound of formula

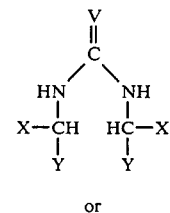
(2a)

or

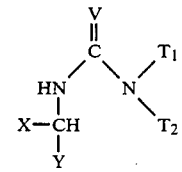
(2b)

or a mixture of the compounds (2a) and (2b) with a compound ZH or a compound of formula

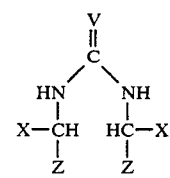
(2c)

or

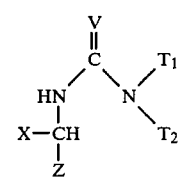
(2d)

or a mixture of the compounds (2c) and (2d) with a compound YH, both reactions under acidic conditions, wherein X and Y are the same or different and each represents an aromatic carbocyclic radical having an unsubstituted or substituted amino group in the para position to the indicated bond, or a heterocyclic group, and Z represents an aryl radical of formula

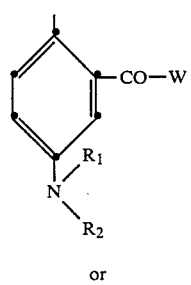
(1a)

or (Abstract continued on next page.)

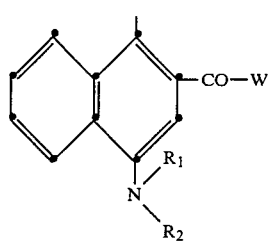

(1b)

wherein
$R_1$ and $R_2$ independently of one another represent hydrogen, $C_1$–$C_{12}$ alkyl, $C_2$–$C_8$-alkoxyalkyl, cycloalkyl, aralkyl, aryl, or substituted alkyl, cycloalkyl, aralkyl or aryl, or $R_1$ and $R_2$ together with the nitrogen atom which links them represent a five- or six-membered, preferably saturated, heterocyclic radical and W represents hydroxy, alkoxy, aryloxy, amino or substituted amino, and the aromatic carbocyclic radical of formula (1a) or (1b) may be further substituted by one or more halogen, cyano, nitro, alkyl of 1 to 4 carbon atoms or alkoxy of 1 to 4 carbon atoms, V represents oxygen, sulphur or imino and $T_1$ and $T_2$ independently represent hydrogen, $C_1$–$C_{12}$-alkyl, $C_2$–$C_{12}$-alkenyl, aryl, aralkyl, and $T_1$ also amido or ureido, or $T_1$ and $T_2$ together with the nitrogen atom which links them represent a five- or six-membered heterocyclic radical.

11 Claims, No Drawings

PROCESS FOR THE PRODUCTION OF TRIARYL METHANE COMPOUNDS

This application is a continuation of application Ser. No. 232,081, filed 2-6-81, now abandoned.

The present invention relates to the production of triaryl methane compounds. More particularly it relates to the production of triaryl methane compounds containing a carbocyclic moiety which contains a carboxylic acid group which, on oxidation, forms a lactone ring, giving a compound which can be used as a colour former.

Accordingly, the invention provides a process for the production of a compound of formula

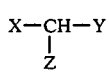  (1)

wherein
  X and Y may be the same or different and each represents an aromatic carbocyclic radical having an unsubstituted or substituted amino group in the para position to the indicated bond, or a heterocyclic group, and
  Z represents an aryl radical of formula

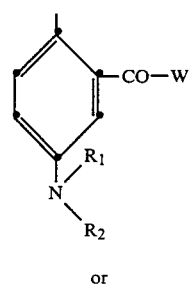  (1a)

or

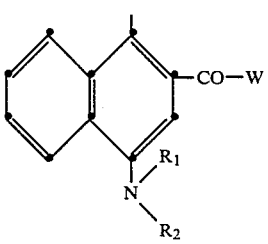  (1b)

wherein
  $R_1$ and $R_2$ independently of one another represent hydrogen, $C_1$–$C_{12}$-alkyl, $C_2$–$C_8$-alkoxyalkyl, cycloalkyl, aralkyl, aryl, or substituted alkyl, cycloalkyl, aralkyl or aryl, or $R_1$ and $R_2$ together with the nitrogen atom which links them represent a five- or six-membered, preferably saturated, heterocyclic radical and
  W represents hydroxy, alkoxy, aryloxy, amino or substituted amino, and the aromatic carbocyclic radical of formula (1a) or (1b) may be further substituted by one or more halogen, cyano, nitro, alkyl of 1 to 4 carbon atoms or alkoxy of 1 to 4 carbon atoms.

The process of the present invention comprises reacting a compound of formula

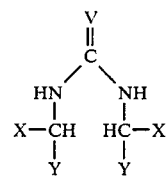  (2a)

or

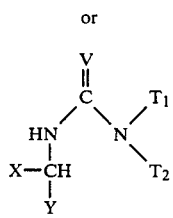  (2b)

or a mixture of the compounds (2a) and (2b) with a compound ZH or a compound of formula

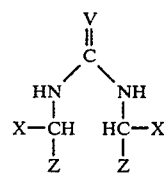  (2c)

or

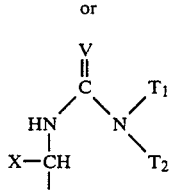  (2d)

or a mixture of the compounds (2c) and (2d) with a compound YH, both reactions under acidic conditions, wherein
  X, Y and Z have the given meanings and
  V represents oxygen, sulphur or imino and
  $T_1$ and $T_2$ independently represent hydrogen, $C_1$–$C_{12}$-alkyl, $C_2$–$C_{12}$-alkenyl, aryl, aralkyl, and $T_1$ also amido or ureido, or
  $T_1$ and $T_2$ together with the nitrogen atom which links them represent a five- or six-membered, preferably saturated, heterocyclic radical.

As an aromatic carbocyclic radical, X and Y may be an amino substituted phenyl radical of formula

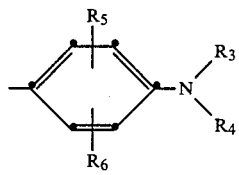  (1c)

wherein $R_3$ and $R_4$ independently represent the groups listed for $R_1$ and $R_2$ above, or together represent methylene groups linked to form a heterocyclic ring which may optionally be interrupted by an oxygen, sulphur or nitrogen atom, and $R_5$ and $R_6$, independently, represent hydrogen, hydroxy, halogen, cyano, nitro, $C_1$–$C_4$-alkyl, $C_1$–$C_4$-alkoxy, $C_2$–$C_8$-alkoxyalkyl, cycloalkyl, aralkyl, aryloxy, arylamino, aryl or a carboxylic acid, carboxylic ester or carboxylic amide group. $R_5$ and $R_6$ are in particular hydrogen, halogen, methyl, methoxy or ethoxy.

As a heterocyclic radical X and Y may represent a mono- or polycyclic (preferably di- or tricyclic) radical containing a 5- or 6-membered heterocyclic ring containing oxygen, sulphur and/or nitrogen as a ring member such as a thienyl, furyl, pyrrolyl, pyrazolyl pyrazolonyl, pyridyl, thiazinyl, oxazinyl, benzothiazinyl, indolyl, indazolyl, benzothiazolyl, benzotriazolyl, naphthotriazolyl, quinolinyl, carbazolyl, phenothiazinyl or phenoxazinyl radical. The mono- or polynuclear heterocyclic radicals may be substituted by one or more of the groups defined for $R_5$ and $R_6$ above.

When X and Y are a heterocyclic radical, this is preferably one of the formula

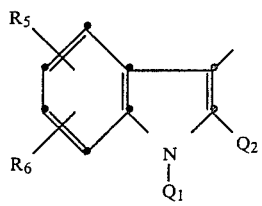

(Id)

wherein $Q_1$ represents hydrogen, $C_1-C_{12}$-alkyl, $C_2-C_{12}$-alkenyl or benzyl and $Q_2$ represents hydrogen, $C_1-C_{12}$-alkyl, or aryl, e.g. phenyl, and $R_5$ and $R_6$ have the given meanings.

When each of the radicals $R_1$ to $R_6$, $T_1$, $T_2$, $Q_1$ and $Q_2$ represent alkyl, they may be straight or branched chain alkyl groups such as methyl, ethyl, n-propyl, isopropyl, n-butyl, sec-butyl, octyl or dodecyl.

When each of the radicals $R_1$ to $R_6$ represent alkoxyalkyl, this may have 1 to 4 carbon atoms in each part, but preferably the alkoxyalkyl radical is β-methoxyethyl or β-ethoxyethyl.

When $Q_1$, $T_1$ and $T_2$ represent alkenyl, this may be for example allyl, 2-methallyl, 2-ethylallyl, 2-butenyl or octenyl. Examples of cycloalkyl in the meaning of the R radicals are cyclopentyl or, preferably, cyclohexyl.

An aryl radical represented by the R and T radicals can be diphenyl, naphthyl or, preferably, phenyl. As aralkyl the R and T radicals may be phenylethyl or, preferably, benzyl.

When $R_1$, $R_2$, $R_3$ and $R_4$ represent substituted alkyl, cycloalkyl, aralkyl or aryl, the substituent may be one or more halogen, hydroxy, cyano, alkyl and/or alkoxy groups, the alkyl or alkoxy substituents having 1 to 4 carbon atoms.

When the pair of substituents ($R_1$ and $R_2$), ($R_3$ and $R_4$) and ($T_1$ and $T_2$), together with the nitrogen atom to which said pair is attached, form a heterocyclic radical, this is for example pyrrolidino, piperidino, pipecolino, morpholino, thiomorpholino or piperazino.

Advantageously $R_1$, $R_2$, $R_3$ and $R_4$, independently, represent hydrogen, $C_1-C_4$-alkyl, $C_2-C_4$-alkoxyalkyl, $C_2-C_4$-cyanoalkyl, cyclohexyl, benzyl or phenyl, or each of the pairs ($R_1$ and $R_2$) and ($R_3$ and $R_4$) together with the nitrogen atom to which said pair is attached, independently, represents pyrrolidino, piperidino or especially morpholino. Preferably, $R_1$, $R_2$, $R_3$ and $R_4$ are methyl.

Z is preferably an aryl radical of formula (1a). W is preferably hydroxy. $T_1$ and $T_2$ are preferably hydrogen.

The reaction to produce compounds of formula (1) from compounds of formula (2a) to (2d) is carried out under acidic conditions. Any non-oxidising strong inorganic or organic acid may be used, for example, hydrochloric, sulphuric, phosphoric, formic, acetic, mono-, di- or trichloroacetic, benzenesulphonic, p-toluene sulphonic or oxalic acid. The acid may be anhydrous or aqueous.

The reaction may optionally be carried out in the presence of an alcoholic solvent, e.g. methanol or ethanol.

The reaction may be carried out at an elevated temperature, e.g. at a temperature from 20° to 100° C., preferably from 80° to 100° C.

The compounds of formulae (2a) to (2d) may be made by various routes, starting from the basic urea, thiourea or guanidine derivative of formula

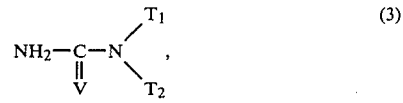

(3)

wherein $R_1$, $T_2$ and V have the given meanings.

This compound may be reacted under acidic conditions with one or two molar equivalents of an aldehyde which is XCHO, YCHO or ZCHO and one or two molar equivalents of a compound XH, YH or ZH having an active hydrogen atom, wherein X, Y and Z have the given meanings. Sufficient acid should be used to protonate the amino groups in the radicals X and Y or X and Z in compounds of formulae (2a) to (2d) above.

This reaction may be carried out between ambient temperature and 100° C., optionally in the presence of an organic solvent, such as an alcohol, e.g. methanol or isopropanol.

Suitable acids include hydrochloric, sulphuric, phosphoric, mono-, di- or trichloroacetic, benzenesulphonic or p-toluenesulphonic acid.

For example, p-dimethylaminobenzaldehyde of formula (4) may be reacted with urea and N,N-dimethylaniline in the presence of an acid to form 1,3-bis[(p-dimethylamino-diphenyl)methyl]urea of formula (5) according to the following scheme

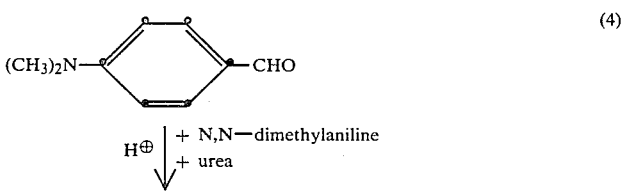

(4)

-continued

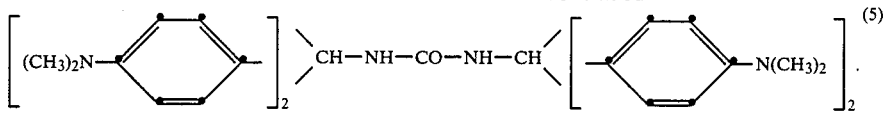 (5)

Generally, a mixture of the compound of the formula (5) and of the compound of formula

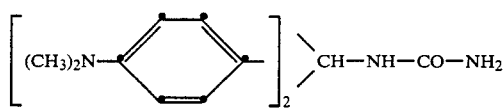 (5a)

is obtained. The weight ratio of the compound of formula (5) to the compound of formula (5a) in advantageously between 1:9 to 9:1, preferably between 1:2 to 2:1.

The resulting compound of formula (5) or the mixture of the compounds of formulae (5) and (5a) can then be reacted with m-dimethylaminobenzoic acid in the presence of an acid to give the leuco triarylmethane of formula

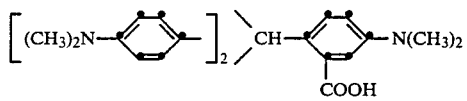 (6)

commonly known as Leuco Crystal Violet Lactone, which on oxidation produces the colour former Crystal Violet Lactone[3,3-(Bis-4'-dimethylamino-phenyl)-6-dimethylaminophthalide].

Instead of the above reaction sequence N,N-dimethylaniline in the first reaction can be replaced by m-dimethylaminobenzoic acid, and in the second reaction N,N-dimethylaniline could be used in place of the m-dimethylaminobenzoic acid.

As a third alternative, in the first reaction, the p-dimethylaminobenzaldehyde may be replaced by the aldehyde of formula

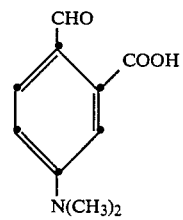 (7)

and in the second reaction, N,N-dimethylaniline could be used in place of the m-dimethylaminobenzoic acid. All three reaction schemes lead to the same product.

In each of the three schemes it is preferred to use an excess of the active hydrogen compound in the first stage and remove the excess by filtration or steam distillation before the second stage is carried out.

The benzaldehyde derivatives used in these reaction schemes can be easily prepared by the so-called Vilsmeier-Haack synthesis (Ber. 1927, 60, 119). It is not always necessary to isolate the aldehyde before reacting it with urea and the active hydrogen compound.

Compounds of formula (2a) in which X and Y are aromatic carbocyclic radicals can also be prepared by reacting the urea compound of formula (3) under acidic conditions optionally in the presence of an organic solvent, such as an alcohol or ketone, e.g. methanol, isopropanol or acetone, with a benzhydrol of formula

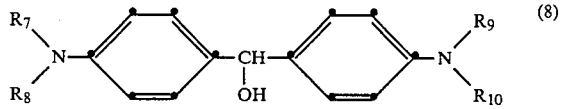 (8)

where the benzene rings may be further substituted by one or more halogen, cyano, nitro, alkyl and/or alkoxy substituents having 1 to 4 carbon atoms, and in which $R_7$, $R_8$, $R_9$ and $R_{10}$ each independently represent $C_1$-$C_{12}$-alkyl, cycloalkyl, aralkyl, aryl, alkoxyaryl, in which the alkoxy group has 2 to 8 carbon atoms, or substituted alkyl, cycloalkyl, aralkyl or aryl.

Sufficient benzhydrol may be used to produce the compound of formula (2a) directly or only enough to react with one $NH_2$—group of the urea may be used. The resulting intermediate may then be reacted with more benzhydrol or with an aldehyde and active hydrogen compound as above to react with the other $NH_2$—group of the urea.

Suitable acids include hydrochloric, sulphuric, phosphoric, formic, mono-, di-, trichloroacetic acid, benzenesulphonic, p-toluene sulphonic or oxalic acid. Mineral acids are preferred on cost grounds.

The resulting compound of formula (2a) is then reacted under acidic conditions with a compound ZH to produce the compound of formula (1).

Since the compounds of formulae (2a) to (2d) can readily be isolated in crystalline form from the reaction mixture, the resulting compounds of formula (1) and colour formers produced from them can be obtained in a very pure form. For example, 4,4'-bis(dimethylamino)benzhydrol (commonly known as Michler's Hydrol) which is used as starting material in the production of Crystal Violet Lactone can contain, when prepared by the oxidation route from 4,4'-bis(dimethylamino-diphenyl)methane, such impurities as the unchanged methane base, tetramethylbenzidine, the corresponding ketone (Michler's ketone) and a hydrol ether. One or more of these impurities are often found in the resulting Crystal Violet Lactone. These impurities, however, are not present when a compound of formulae (2a) to (2d) is used and hence do not appear in the final product. An impurity that may be formed concurrent with a compound of the formulae (2a) to (2d) is Leuco Crystal Violet. As this may have a detrimental effect on the properties of Crystal Violet Lactone it is an advantage to remove this compound. This impurity can readily be removed by solvent extraction with a water immiscible solvent, e.g. an aromatic hydrocarbon such as toluene, either on the compounds of formulae (2a) to (2d) themselves or on the aqueous alkaline solution of Leuco Crystal Violet Lactone prepared from compounds (2a) to (2d). If this treatment is carried out then Crystal Violet Lactone need not be recrystallised from an organic solvent (with consequent loss in yield) to obtain it in the necessary state of purity for use as a colour former.

A further advantage of the process of the invention is that the products of formula (1) are obtained in higher yields than by conventional methods.

In the examples which follow, the percentages quoted relate to weight, unless otherwise indicated.

EXAMPLE 1

32 g of 4-Dimethylaminobenzaldehyde are dissolved in 95 ml of 28% hydrochloric acid, 6 g of urea are added at room temperature followed by 31,5 g of N,N-dimethylaniline. Afterwards the mixture is stirred at room temperature until the reaction has finished. The reaction mixture is then added drop-wise with good agitation to excess iced water containing 100 ml of ammonia 30%. The excess N,N-dimethylaniline is removed by steam distillation (keeping the distillation mass alkaline to Brilliant Yellow paper throughout by addition of sodium hydroxide solution as required). The aqueous distillation residue is cooled to room temperature. The afforded 1,3-bis(4',4"-dimethylamino-diphenyl-methyl)urea is filtered off, washed with methanol and water, and dried: yield 50 g.

The urea derivative from above is charged into 345 ml of sulphuric acid 10.5% wt/vol. 30 g of m-dimethylaminobenzoic acid are added and the mixture is heated at 95°–100° C. for 3 hours. The reaction mixture is then cooled to 5° C. by the addition of ice/water and the pH adjusted to around 5 with ammonia 30% (ca 45 ml). The mixture is stirred for 45 minutes then heated to 75° C. and maintained at 75° C. for 30 minutes. The resulting 2-(4,4'-bis-dimethylaminobenzhydryl)-5-dimethylaminobenzoic acid (Leuco Crystal Violet Lactone) is filtered off and washed sulphate-free with hot water and dried: yield 58 g.

EXAMPLE 2

185 g of phosphorus oxychloride are added with good agitation over 1–2 hours at or below 25° C. to 110 g of dry dimethylformamide and the complex is stirred for a further 15 minutes. Then 140 g of N,N-dimethylaniline are run in over 2 hours at or below 45° C. and the mixture is stirred for 30 minutes and then heated to 100° C. and maintained at 100° C. for 2 hours and cooled to 50° C. 70 g of ice are added carefully, followed by 105 g of hydrochloric acid (36%) and 30 g of urea and the whole is stirred for 15 minutes. Afterwards 157,5 g of N,N-dimethylaniline are run in and the mixture is stirred overnight at room temperature, then heated to 60° C. and maintained at 60° C. for 2 hours. 760 g of iced water are then added and the mixture is neutralised with aqueous sodium hydroxide. The resulting mixture of 1,3-bis(4',4"-dimethylaminodiphenylmethyl)urea and 1-(4',4"-dimethylamino-diphenylmethyl)urea (1:1) is filtered off, washed with methanol and water and dried: yield 225 g. The resulting urea derivative mixture is converted into Leuco Crystal Violet Lactone by reaction with m-dimethylamino benzoic acid as described in Example 1.

EXAMPLE 3

10,8 g of 4,4'-bis(dimethylamino)benzhydrol, in the form of a technical quality aqueous paste, 1.2 g of urea and 0.7 g of sulphuric acid 98% are added to 100 ml of methanol and the mixture is stirred overnight at ambient temperature. The reaction mass is neutralised with dilute ammonia and the resulting mixture of 1,3-bis(4',4"-dimethylamino-diphenyl-methyl)urea and 1-(4',4"-dimethylamino-diphenyl-methyl)urea is filtered off, washed with methanol, with water and dried, (yield: 11.4 g). The resulting urea derivative mixture is converted into Leuco Crystal Violet Lactone by reaction with m-dimethylaminobenzoic acid as described in Example 1.

EXAMPLE 4

32 g of 4-dimethylamino-benzaldehyde and 6 g of urea are added to 95 ml hydrochloric acid 28%. The mixture is cooled to 15° C. and stirred to dissolve. Afterwards 39 g of m-dimethylaminobenzoic acid are added and the mixture is heated at 100° C. until no further reaction occurs. 95 ml of water are added and the aqueous mixture is neutralised with sodium hydroxide. The mixture of 1,3-bis[4'-dimethylamino-phenyl-(4"-dimethylaminophenyl-2"-carboxylic acid)methyl]urea and 1-(4'-dimethylamino-phenyl-(4"-dimethylamino-phenyl-2"-carboxylic acid)methyl]urea (1:1) is filtered off and washed succesively with water, methanol and water and dried: yield 7 g. The urea derivative mixture is then converted into Leuco Crystal Violet Lactone by reaction with 2.8 g of N,N-dimethylaniline by the procedure described in Example 1.

EXAMPLE 5

11,8 g of 4-diethylaminobenzaldehyde are dissolved in 60 ml 15% hydrochloric acid, 4,03 g of urea added and the solution stirred for 1 hour at room temperature. 9,8 g of N,N-diethylaniline are then added, the pH adjusted to 1,5 and the mixture stirred at 70° C. for 50 hours. After cooling to room temperature 30% sodium hydroxide solution is added to pH 9.5, followed by 20 ml of toluene. After stirring for 30 minutes the precipitated 1,3-bis(4',4"-diethylaminodiphenylmethyl)urea is filtered off, washed with ether and dried: yield 11,0 g.

1,8 g of 3-dimethylaminobenzoic acid are suspended in 50 ml of water at 80° C. and the pH adjusted to 1.8 by the addition of 96% sulphuric acid. 3,69 g of the above urea derivative are then added, the pH again adjusted to 1.8 and the solution stirred overnight at 80° C. After cooling to 0° C., the mixture is neutralized with 30% ammonia solution, the precipitated 2-(4,4'-bis-diethylaminobenzhydryl)-5-dimethylaminobenzoic acid filtered off, washed with water and dried: yield 4,0 g.

EXAMPLE 6

7,6 g of phosphorus oxychloride are added dropwise with cooling below 20° C. to 8,7 g of dimethylformamide. 16,3 g of N-phenylmorpholine are then added in portions over 6 hours below 45° C. The mixture is stirred for a further 1 hour at 65° C. and for a further 1 hour at room temperature. 10 ml of ice-water are then added below 40° C. followed by 3,0 g of urea. The mixture is stirred for 50 hours at room temperature, 30% sodium hydroxide solution added to pH 7 followed by 20 ml of toluene. After stirring for 1 hour at room temperature, the precipitated 1,3-bis-(4',4"-morpholinodiphenylmethyl)urea is filtered, washed with ether and dried: yield 14,0 g. 3,96 g of this urea derivative are then reacted with 1,8 g of 3-dimethylaminobenzoic acid as described in Example 5 to yield 3,0 g of 2-(4,4'-di-N-morpholinobenzhydryl)-5-dimethylaminobenzoic acid.

EXAMPLE 7

A solution of 2,5 g 4-dimethylaminobenzaldehyde and 0,95 g of urea in 7,5 ml of 18% hydrochloric acid is stirred for 1 hour at room temperature, 3,3 g of N-benzyl-N-methylaniline added, and the mixture stirred overnight at room temperature. Ice is then added followed by 30% sodium hydroxide solution to pH 9.5. The 1,3-bis(4'-N-benzyl-N-methylamino-4''-dimethylaminodiphenylmethyl)urea is obtained as an oil, which is separated, washed with water and dried: yield 4,0 g.

2,0 g of the urea derivative are reacted with 0,93 g of 3-dimethylaminobenzoic acid in the same manner as described in Example 5, to yield 1,5 g of 2-(4-N-benzyl-N-methylamino-4'-dimethylaminobenzhydryl)-5-dimethylaminobenzoic acid.

EXAMPLE 8

29,8 g of 4-dimethylaminobenzaldehyde are dissolved in 85 g of 18% hydrochloric acid, 9,9 g of thiourea added and the mixture stirred for 1 hour at room temperature. 24,2 g of dimethylaniline are added dropwise over 20 minutes and the mixture stirred overnight at room temperature. After pouring onto ice, 30% sodium hydroxide solution is added to pH 7 and the resulting emulsion steam distilled. The residue is cooled and the 1,3-bis-(4',4''-dimethylaminodiphenylmethyl)thiourea filtered off, washed with methanol and dried: yield 12,0 g.

6,0 g of the thiourea derivative are then converted into Leuco Crystal Violet Lactone by reaction with 3,3 g of 3-dimethylaminobenzoic by the procedure described in Example 1.

EXAMPLE 9

Following the procedure of Example 8, but using 12,4 g of guanidin hydrochloride in place of thiourea, 14,1 g of 1,3-bis-(4',4''-dimethylaminodiphenylmethyl)-guanidin are obtained. 7,0 g of the guanidin derivative are then converted into Leuco Crystal Violet Lactone by reaction with 4,0 g of 3-dimethylaminobenzoic acid according to the procedure of Example 1.

EXAMPLE 10

14,9 g of 4-Dimethylaminobenzaldehyde are dissolved in 70 g of 18% hydrochloric acid, 17,7 g of N-phenylurea added and the mixture stirred for 1 hour at room temperature. 12,1 g of dimethylaniline are then added over 20 minutes and the mixture stirred overnight at room temperature. The resulting suspension is poured onto ice and neutralised to pH 7 by the addition of 30% sodium hydroxide solution. The precipitate is filtered, washed with water, slurried in 125 ml of toluene, filtered, washed with toluene and dried to yield 15,1 g of 1-(4',4''-dimethylaminodiphenylmethyl)-3-phenyl urea. 7,5 g of the urea derivative are converted into Leuco Crystal Violet Lactone by reaction with 3,3 g of 3-dimethylaminobenzoic acid by the procedure described in Example 1.

EXAMPLE 11

Substituting the N-phenyl urea by 9,6 g of N-methyl urea and following the procedure of Example 10, 18,1 g of 1-(4',4''-dimethylaminodiphenylmethyl)-3-methyl urea are obtained. 8,9 g of this urea derivative are converted into Leuco Crystal Violet Lactone by reaction with 5,0 g of 3-dimethylaminobenzoic acid according to the procedure of Example 1.

EXAMPLE 12

Leuco Crystal Violet, if present, can be removed from Leuco Crystal Violet Lactone in the following manner. 20,4 of Leuco Crystal Violet Lactone obtained as described in any of Examples 1 to 4 are are added to 200 ml water and 3,0 g of sodium hydroxide are added. The reaction mixture is stirred, heated to 80° C., and maintained until dissolution occurs. This solution is extracted with toluene to remove Leuco Crystal Violet. The resulting aqueous solution of purified Leuco Crystal Violet Lactone can now be oxidised in the usual manner to give Crystal Violet Lactone.

What is claimed is:

1. A process for the production of a leuco compound of the formula

which comprises the steps of preparing either an intermediate of the formula

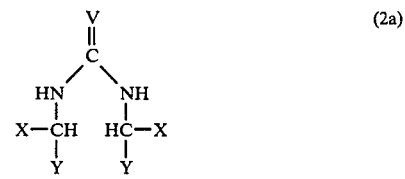

or

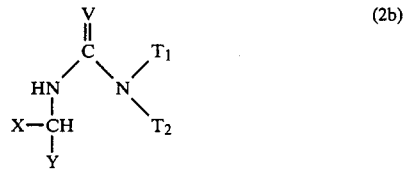

or a mixture of the compounds (2a) and (2b), or an intermediate of the formula

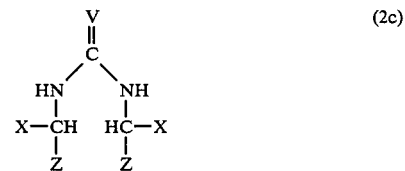

or

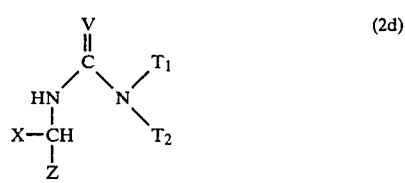

or a mixture of compounds (2c) and (2d) by reacting under strong, non-oxidizing acidic conditions an urea derivative of the formula

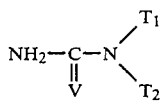

with one or two moles of an aldehyde X—CHO, Y—CHO or Z—CHO plus an equimolar amount of a compound X—H, Y—H or Z—H having an activated hydrogen atom, isolating said intermediate or mixture of intermediates, and then reacting said intermediate or mixture of intermediates with a compound of the formula Z—H or Y—H having an activated hydrogen atom under strong non-oxidizing acidic conditions, wherein Z represents an aryl radical of the formula

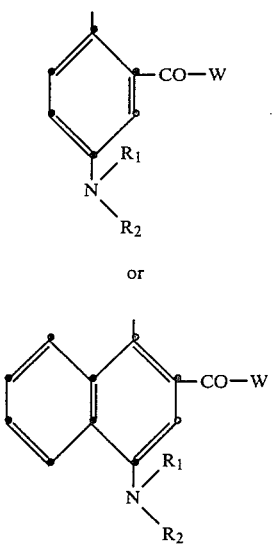

and X and Y are the same or different and each represents an amino substituted phenyl radical of the formula

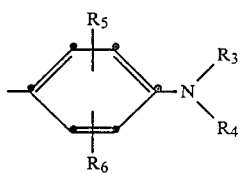

or an indolyl radical of the formula

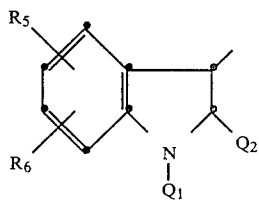

wherein $R_1$, $R_2$, $R_3$, $R_4$ independently represent hydrogen, $C_1$-$C_4$-alkyl, $C_2$-$C_4$-alkoxyalkyl, $C_2$-$C_4$-cyanoalkyl, cyclohexyl, benzyl or phenyl, or each pair of substituents ($R_1$ and $R_2$) and ($R_3$ and $R_4$) together with the nitrogen atom to which said pair is attached represents pyrrolidino, piperidino or morpholino and $R_5$ and $R_6$ independently are hydrogen, halogen, methyl, methoxy or ethoxy, $Q_1$ represents hydrogen, $C_1$-$C_{12}$-alkyl, $C_2$-$C_{12}$-alkenyl or benzyl, $Q_2$ represents hydrogen, $C_1$-$C_{12}$-alkyl or phenyl, W represents hydroxy, alkoxy, phenyloxy or amino, V represents oxygen, sulphur or imino and $T_1$ and $T_2$ independently represent hydrogen, $C_1$-$C_{12}$-alkyl, $C_2$-$C_{12}$-alkenyl, phenyl or benzyl, or $T_1$ and $T_2$ together with the nitrogen atom which links them represent pyrrolidino, piperidino, pipecolino, morpholino, thiomorpholino or piperazino.

2. A process of claim 1, wherein the compound of formula (2a) or (2b) is reacted with the compound of the formula Z—H, or the compound of formula (2c) or (2d) is reacted with the compound of formula Y—H.

3. A process of claim 1, wherein X and Y are each an amino substituted phenyl radical of formula

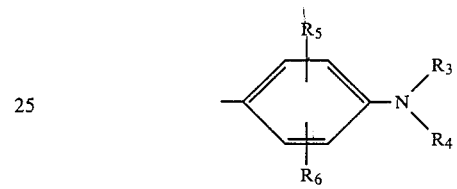

4. A process of claim 1, wherein $R_1$, $R_2$, $R_3$ and $R_4$ are each methyl.

5. A process of claim 1, wherein Z is an aryl radical of formula (1a) and W is hydroxy.

6. A process of claim 1 wherein X and Y independently are each an indolyl radical of the formula

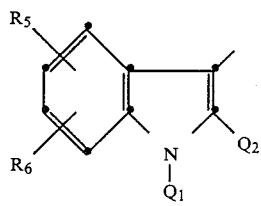

7. A process of claim 1 wherein a mixture of the compounds of formulae (2a) and (2b) is used.

8. A process of claim 1, wherein $T_1$ and $T_2$ are hydrogen.

9. A process of claim 1 wherein p-dimethylaminobenzaldehyde is reacted with urea and N,N-dimethylaniline in the presence of an acid to form N-[4,4'-dimethylamino-diphenyl-methyl]urea or N,N'-bis[4,4'-dimethylamino-diphenyl-methyl]urea or a mixture of these urea derivatives.

10. A process of claim 1 wherein N-[4,4'-dimethylamino-diphenyl-methyl]urea or N,N'-bis[4,4'-dimethylamino-diphenyl-methyl]urea or a mixture thereof is reacted with m-dimethylaminobenzoic acid in the presence of an acid to give 2-(4',4''-bis-dimethylamino-benzhydryl)-5-dimethylamino benzoic acid.

11. A process of claim 1 wherein the second reaction step is carried out at a temperature of 20° to 100° C.

* * * * *